United States Patent [19]

Michalowicz

[11] 4,021,487
[45] May 3, 1977

[54] PREPARATION OF m-AMINO-α-METHYLBENZYL ALCOHOL

[75] Inventor: William Michalowicz, Lock Haven, Pa.

[73] Assignee: American Color & Chemical Corporation, Charlotte, N.C.

[22] Filed: May 24, 1974

[21] Appl. No.: 473,229

[52] U.S. Cl. .................................. 260/580; 250/545
[51] Int. Cl.$^2$ ......................................... C07C 85/11
[58] Field of Search ........................... 260/580, 575

[56] References Cited
UNITED STATES PATENTS

| 2,683,745 | 7/1954 | Emerson et al. | 260/580 X |
| 2,797,244 | 6/1957 | Tinsley | 260/580 |
| 3,079,435 | 2/1963 | Freifelder et al. | 260/580 X |
| 3,274,249 | 9/1966 | Brunner et al. | 260/580 X |
| 3,423,462 | 1/1969 | Rylander | 260/580 |

OTHER PUBLICATIONS

House, Modern Synthetic Reactions, W. A. Benjamin, Inc. California, 2nd Ed. pp. 1–8 (1972).

*Primary Examiner*—Helen M. S. Sneed
*Attorney, Agent, or Firm*—Armstrong, Nikaido & Marmelstein

[57] ABSTRACT m-Amino-α-methylbenzyl alcohol is produced in a facile manner in a single step hydrogenation from m-nitroacetophenone under relatively mild conditions with a palladium catalyst, through the utilization of a strongly acidic aqueous medium.

4 Claims, No Drawings

PREPARATION OF m-AMINO-α-METHYLBENZYL ALCOHOL

BACKGROUND OF THE INVENTION

In the preparation of dyestuffs, m-amino-α-methylbenzyl alcohol is a useful intermediate which can be readily introduced into chromophoric molecules to produce useful dyestuffs. For example, m-amino-α-methylbenzyl alcohol may be condensed with haloanthraquinones to yield arylaminoanthraquinones which, when devoid of water solubilizing groups such as sulfo and carboxy, find utility in the field of polyester dyestuffs. In spite of the fact that such end product anthraquinones would be good dyestuff, their use has been somewhat restricted by the difficulty of obtaining the necessary starting material, m-amino-α-methylbenzyl alcohol, in a facile, inexpensive manner. Various researchers have reported on new ways for the synthesis of a m-amino-α-methylbenzyl alcohol, but for the reasons set forth hereinbelow there are numerous drawbacks to such methods.

There are numerous reports in the literature of the hydrogenation of m-nitroacetophenone to m-aminoacetophenone under a relatively low hydrogen pressure such as 2-5 atoms, in various solvents using the common hydrogenation catalysts such as nickel, palladium, and platinum. Reports of such research are found in Chemical Abstracts, 46, 10180i; 47, 5380e; 55, 25795e; and British Pat. No. 1,104,168. Such methods suffer from drawbacks, however, in that the second stage hydrogenation of the intermediate m-aminoacetophenone to the desired m-amino-α-methylbenzyl alcohol is reported only under extreme conditions such as 2000 psi to 4700 psi at 120° to 155° C, as reported in British Pat. No. 758,993 and U.S. Pat. No. 2,680,136. Thus, the prior art method requiring a two-step hydrogenation and the use of very extreme conditions in the second stage represents a distinct drawback to the worker of ordinary skill in the art faced with the problem of producing economical intermediate products for the synthesis of dyestuffs.

In British Pat. No. 758,993 there is described a proposal for the one-step catalytic preparation of m-amino-α-methylbenzyl alcohol from m-nitroacetophenone, but a pressure of 2000 psi at 120° C is required, Raney nickel being used in a dioxane solvent. A two stage process is discussed in U.S. Pat. No. 2,680,136 where m-nitroacetophenone is first catalytically reduced to m-amino-acetophenone under mild conditions which utilizes Raney nickel. However, the second stage requires the use of high pressure on the order of 4700 psi to 4800 psi with a copper chromite catalyst at a temperature of in excess of 150° C.

From the foregoing, it is seen that most of the prior art processes discussed herein require a two stage treatment. Furthermore, the prior art processes teach the conversion of the starting or intermediate material to m-amino-α-methylbenzyl alcohol only under extreme conditions of pressure.

It is also known that m-amino-α-methylbenzyl alcohol, being a benzyl alcohol, is subject to possible hydrogenolysis in the presence of a certain hydrogenolysis catalysts to m-ethyl-aniline. The facile hydrogenolysis of benzyl alcohols (cleavage of the benzyl-oxygen bond) is well recognized and the reaction description appears in standard texts on catalytic hydrogenation (e.g. Catalytic Hydrogenation, R. L. Augustine, Marcel Dekker, Inc., N. Y. 1965, chapter 6: Catalytic Hydrogenation Over Platinum Metals, P. N. Rylander, Academic Press, N. Y. 1967, chapter 15 and 25). According to these texts, benzylic oxygen is readily cleaved with a palladium catalyst. Furthermore, mineral acids greatly facilitate such cleavage.

SUMMARY OF THE INVENTION

According to the present invention m-amino-α-methyl-benzyl alcohol is produced in high yield in the presence of a palladium catalyst and a mineral acid. The m-Amino-α-methylbenzyl alcohol is produced by treating m-nitroacetophenone in an aqueous medium containing a mineral acid with hydrogen, said hydrogen being under pressure of from 25 psi to about 1000 psi, in the presence of from about 0.5 to 2.5 parts per 100 parts of m-nitro-acetophenone of 5% palladium on carbon catalyst. The reaction is conducted at a temperature of below 50° C.

DETAILED DESCRIPTION OF THE INVENTION

The m-Nitroacetophenone is suspended in an aqueous medium and a mineral acid (sulfuric or phosphoric acid) is added, the molar ratio of the acid to m-nitroacetophenone being from 1:2 to 2:1. The concentration of the m-nitroacetophenone initially suspended in the aqueous medium does not appear to be critical to the success of the reaction. Thus its concentration is limited only by practical considerations such as economics and ease of handling of the system.

Good results have been obtained when the system is hydrogenated with a 5% palladium on carbon catalyst. The amount of this catalyst used is preferably from about 0.5 to about 2.5 parts per 100 parts of m-nitroacetopheone. It is expected that other forms of palladium catalysts may be used in the invention; the amount of palladium, per se, suitable being that amount corresponding to the amount of palladium present in 0.5 to 2.5 parts of a 5% palladium on carbon catalyst. The hydrogen pressure may vary from 25 psi to 1000 psi, the preferred range being from 100 psi to 300 psi. The temperature must be maintained below 50° C to achieve the high yields and purity of product, the preferred range being 25° to 40° C. If the temperature is allowed to exceed the stated range, hydrogenolysis of the desired product occurs. The hydrogen absorption will self terminate when the reaction is complete, the time required generally being from 2 to 4 hours. The resulting product, m-amino-α-methylbenzyl alcohol, which remains in the reaction solution can be isolated by any of several standard techniques, e.g. neutralization and subsequent salting out; solvent extraction; removal of solvent; etc.

The purity of the m-nitroacetophenone, too, does not appear to be critical and so-called crude m-nitroacetophenone containing minor amounts of acidic impurities may be employed.

EXAMPLE I m-Nitroacetophenone [99.0 g., 0.60 mole, 100% purity by GLC (gas-liquid chromatography)], water containing 0.30 mole of sulfuric acid (420 ml.), and 5% palladium on carbon (1.0 g., Englehard) were charged to a 1 liter Parr stirring autoclave. The hydrogen pressure was raised to 180 psi. As hydrogenation progressed, the pressure decreased to 30 psi whereupon the pressure was again raised to 180 psi. This repressuring was continued until hydrogen absorption ceased (4 hours). The temperature was maintained at 25° to 40° C during the hydrogenation. The filtered hydrogenate was neutralized, with cooling, with 50% sodium hydroxide (0.60 mole used). The resulting emulsion was stirred in a cooling bath until crystallization was complete. The crystalline product was removed and the filtrate was evaporated under vacuum to leave a solid residue. Both products were extracted with acetone and analyzed by GLC.

Yield from crystalline product: 76.4 g., 3.9% m-ethylaniline 96.1% m-amino-α-methylbenzyl alcohol Yield from filtrate: 4.6 g., 100% m-amino-α-methylbenzyl alcohol for a total crude yield of 98.5%.

EXAMPLE II m-Nitroacetophenone (66.0 g., 0.40 mole), water containing 0.30 mole sulfuric acid (300 ml.), and 5% palladium on carbon (2.0 g.) were hydrogenated under 300 psi to 200 psi as in Example I at 25° to 36° C. After hydrogen absorption ceased (2 hours), the hydrogenate, after filtration, was neutralized with 50% sodium hydroxide and allowed to crystallize as in Example I. The product was obtained in 86% yield and was found to be 99% m-amino-α-methylbenzyl alcohol by GLC, with a melting point of 66° C to 67° C.

EXAMPLE III m-Nitroacetophenone (82.3 g., 0.50 mole), water containing 0.85 mole of phosphoric acid (300 ml.), and 5% palladium on carbon (1.5 g.) were charged and hydrogenated as in Example II. The resulting hydrogenate was neutralized with 45% potassium hydroxide (1.70 mole) and stirred in a cooling bath until precipitation of solids was complete. m-Amino-α-methylbenzyl alcohol was obtained in 86% yield and contained 97.8% pure product with 2.2% m-ethylaniline.

EXAMPLE IV m-Nitroacetophenone (66.0 g., 0.40 mole), water containing 0.70 mole phosphoric acid (300 ml.), and 5% palladium on carbon (2.0 g.) were hydrogenated as in Example II until hydrogen absorption ceased (2 hours). Work-up after neutralization with 1.40 moles potassium hydroxide gave m-amino-α-methylbenzyl alcohol in 75% yield which was 99% pure by GLC and contained 0.8% m-ethylaniline.

Although the invention has been described with reference to certain preferred embodiments thereof it is understood that it is not to be limited thereto, but on the contrary, is intended to include all those embodiments within the scope and spirit of the appended claims.

What is claimed is:

1. A process for producing m-amino-α-methylbenzyl alcohol from m-nitroacetophenone in a single step process comprising hydrogenating m-nitroacetophenone in a highly acidic aqueous reaction system consisting essentially of water, a mineral acid and a catalytic amount of a 5% palladium on carbon catalyst, the molar ratio of acid to m-nitroacetophenone being from 1:2 to 2:1; said hydrogenation being carried out at a temperature of less than about 50° C and at a hydrogen pressure of from 25 psi to about 1000 psi.

2. A process for producing m-amino-α-methylbenzyl alcohol from m-nitroacetophenone in a single step process comprising hydrogenating m-nitroacetophenone in a highly acidic aqueous reaction system consisting essentially of water, a mineral acid and a catalytic amount of a 5% palladium on carbon catalyst, the molar ratio of acid to m-nitroacetophenone being from 1:2 to 2:1; said hydrogenation being carried out at a temperature of less than about 50° C and at a hydrogen pressure of from 25 psi to about 300 psi.

3. The process of claim 2 wherein the acid is sulfuric acid or phosphoric acid.

4. The process of claim 2 wherein the treating is conducted at a temperature of from 25° to 40° C.

* * * * *